(12) United States Patent
Crozet

(10) Patent No.: US 7,799,062 B2
(45) Date of Patent: Sep. 21, 2010

(54) SELF-GUIDING THREADED FASTENER

(75) Inventor: Yves Crozet, Bellach (CH)

(73) Assignee: Stryker Trauma S.A. (CH)

( * ) Notice: Subject to any disclaimer, the term of this patent is extended or adjusted under 35 U.S.C. 154(b) by 1062 days.

(21) Appl. No.: 11/000,098

(22) Filed: Nov. 30, 2004

(65) Prior Publication Data

US 2006/0116686 A1 Jun. 1, 2006

(51) Int. Cl.
*A61B 17/86* (2006.01)

(52) U.S. Cl. .................. 606/315; 606/311; 606/312

(58) Field of Classification Search .............. 606/281, 606/291, 300, 309, 311, 312, 315; 411/85, 411/412

See application file for complete search history.

(56) References Cited

U.S. PATENT DOCUMENTS

| 1,007,107 | A |   | 10/1911 | Hulsmann |
|-----------|---|---|---------|----------|
| 1,980,093 | A | * | 11/1934 | Rosenberg ............ 411/412 |
| 3,466,748 | A |   | 9/1969  | Christensen |
| 3,918,345 | A |   | 11/1975 | Phipard, Jr. |
| 4,040,328 | A |   | 8/1977  | Muenchinger |
| 4,319,420 | A |   | 3/1982  | Clinton |
| 4,429,600 | A |   | 2/1984  | Gulistan |
| 4,544,313 | A |   | 10/1985 | Grossberndt |
| 4,940,467 | A |   | 7/1990  | Tronzo |
| 4,966,599 | A |   | 10/1990 | Pollock |
| 5,019,103 | A |   | 5/1991  | Van Zile et al. |
| 5,139,499 | A |   | 8/1992  | Small et al. |
| 5,141,376 | A |   | 8/1992  | Williams et al. |
| 5,180,382 | A |   | 1/1993  | Frigg et al. |
| 5,199,873 | A | * | 4/1993  | Schulte et al. .............. 433/174 |
| 5,242,253 | A |   | 9/1993  | Fulmer |

(Continued)

FOREIGN PATENT DOCUMENTS

AU        4206789        4/1990

(Continued)

OTHER PUBLICATIONS

Partial European Search Report, EP 05 40 5411, Dated Mar. 13, 2006.

*Primary Examiner*—Thomas C Barrett
*Assistant Examiner*—Andrew Yang
(74) *Attorney, Agent, or Firm*—Lerner, David, Littenberg, Krumholz & Mentlik, LLP

(57) ABSTRACT

A screw fastener for attachment to an orthopedic component such as an orthopedic plate for use in connection with fracture fixation, joint reconstruction or spinal stabilization or fusion is disclosed as having a shank with at least two different shank diameters, one in a plate engaging portion of the shank and one in the bone or other component engaging portion of the shank. At least two of the different shank diameters on the shank include threads, the threads on the two different diameter portions each having substantially the same thread height and pitch. A plate having a threaded aperture, or an adapter having a threaded aperture, is sized such that the threads of the smaller diameter shank portion engage and cooperate with the internal threads of the aperture to correctly align the screw fastener and the implant as the screw fastener is threaded through the implant. The threads on the larger diameter shank portion and the internal threads of the aperture of the implant are sized so that the threads of the larger diameter shank portion are fully engaged with the internal threads of the orthopedic implant.

23 Claims, 5 Drawing Sheets

U.S. PATENT DOCUMENTS

| | | | |
|---|---|---|---|
| 5,246,441 A | 9/1993 | Ross et al. | |
| 5,259,398 A | 11/1993 | Vrespa | |
| 5,360,448 A | 11/1994 | Thramann | |
| 5,364,400 A | 11/1994 | Rego, Jr. et al. | |
| 5,385,439 A | 1/1995 | Hurdle | |
| 5,456,685 A | 10/1995 | Huebner | |
| 5,591,166 A | 1/1997 | Bernhardt et al. | |
| 5,697,929 A | 12/1997 | Mellinger | |
| 5,795,120 A | 8/1998 | Hurdle | |
| 5,797,914 A | 8/1998 | Leibinger | |
| 5,915,967 A | 6/1999 | Clokie et al. | |
| 5,925,048 A | 7/1999 | Ahmad et al. | |
| 5,951,560 A | 9/1999 | Simon et al. | |
| 5,964,768 A | 10/1999 | Huebner | |
| 5,997,541 A | 12/1999 | Schenk | |
| 6,030,162 A | 2/2000 | Huebner | |
| 6,048,344 A | 4/2000 | Schenk | |
| 6,086,303 A | 7/2000 | Fluckiger | |
| 6,120,227 A | 9/2000 | Murase et al. | |
| 6,123,711 A | 9/2000 | Winters | |
| 6,129,730 A | 10/2000 | Bono et al. | |
| 6,149,653 A | 11/2000 | Deslauriers | |
| 6,273,889 B1 | 8/2001 | Richelsoph | |
| 6,306,140 B1 | 10/2001 | Siddiqui | |
| 6,322,562 B1 * | 11/2001 | Wolter | 606/62 |
| 6,355,043 B1 | 3/2002 | Adam | |
| 6,454,771 B1 | 9/2002 | Michelson | |
| 6,488,681 B2 | 12/2002 | Martin et al. | |
| 6,527,776 B1 | 3/2003 | Michelson | |
| 6,554,834 B1 | 4/2003 | Crozet et al. | |
| 6,565,573 B1 | 5/2003 | Ferrante et al. | |
| 6,585,740 B2 | 7/2003 | Schlapfer et al. | |
| 6,616,666 B1 | 9/2003 | Michelson | |
| 6,620,163 B1 | 9/2003 | Michelson | |
| 6,730,091 B1 * | 5/2004 | Pfefferle et al. | 606/70 |
| 6,875,215 B2 * | 4/2005 | Taras et al. | 606/916 |
| 6,955,677 B2 * | 10/2005 | Dahners | 606/287 |
| 7,001,389 B1 * | 2/2006 | Navarro et al. | 606/71 |
| 7,179,260 B2 * | 2/2007 | Gerlach et al. | 606/291 |
| 2001/0001119 A1 | 5/2001 | Lombardo | |
| 2002/0016594 A1 | 2/2002 | Schlapfer et al. | |
| 2002/0016595 A1 | 2/2002 | Michelson | |
| 2002/0052605 A1 | 5/2002 | Grooms et al. | |
| 2002/0058939 A1 * | 5/2002 | Wagner et al. | 606/61 |
| 2002/0183748 A1 | 12/2002 | Martin et al. | |
| 2003/0074002 A1 | 4/2003 | West | |
| 2003/0088251 A1 | 5/2003 | Braun et al. | |
| 2003/0158556 A1 | 8/2003 | Taras et al. | |
| 2003/0181912 A1 | 9/2003 | Michelson | |
| 2003/0187447 A1 | 10/2003 | Ferrante et al. | |
| 2006/0116686 A1 | 6/2006 | Crozet | |
| 2006/0149265 A1 | 7/2006 | James et al. | |

FOREIGN PATENT DOCUMENTS

| | | |
|---|---|---|
| DE | 298 09 736 U1 | 6/1998 |
| DE | 198 52 945 A1 | 3/2000 |
| EA | 0 554 915 A | 8/1993 |
| EP | 0 387 392 | 9/1990 |
| EP | 0 705 572 A | 4/1996 |
| EP | 1 145 691 A | 10/2001 |
| FR | 2 704 170 A1 | 4/1993 |
| FR | 2 739 151 A1 | 9/1995 |
| JP | 4-295348 | 10/1992 |
| WO | WO-02/065925 A1 | 8/2002 |

* cited by examiner

SELF-GUIDING THREADED FASTENER

BACKGROUND OF THE INVENTION

The present invention relates to the fixation of orthopedic implants, including fasteners to bones and other orthopedic devices and fasteners for effecting such fixation, as well as associated methods.

Orthopedic surgery, whether it be for fracture fixation, joint reconstruction, spine stabilization or fusion, often comprises the fastening of an implant, including an orthopedic plate, to a bone or to another implant or component of a trauma, reconstructive or fusion system. Typically, a screw fastener is used in conjunction with an aperture in an orthopedic implant, and the threads of the screw fastener engage bone or another component of the system as indicated above. In some cases, particularly with respect to certain orthopedic implants that are to be fixed to a bone to treat a fracture, to aid in joint reconstruction or to aid in stabilization or fusion of vertebral bodies, the screw fastener would include not only threads to engage the bony material, but also threads to engage the female threads in a threaded aperture. The engagement of threads between an orthopedic plate, for instance, and the head portion of the screw fastener shank, if any, increases the post-operative strength and stiffness of the plating construct. Such plate-engaging threads help prevent back-out of the screw fastener.

In order to accomplish the goal of fixing orthopedic plates to the bone, orthopedic screws have been constructed with threads designed for engaging bony structures. This enables the screw to be tightly positioned against the plate and bone. In such a design, the aperture of the orthopedic plate in which the screw is received often includes internal threads for coupling the bone screw to the orthopedic implant. Since many screws are designed to specifically have threads which are best adapted for anchoring in bony material, often the engagement between the screw and the orthopedic plate is not optimized.

Prior art designs have attempted to solve this problem by constructing fasteners that have two different threads extending outwardly from a shank. For example, the part of the shank which is designed to be disposed within the bone may include external threads specifically adapted to engage bony material. The part of the shank designed to be disposed within the apertures of the orthopedic plate—i.e., the plate-engaging portion of the shank—includes a second external thread designed to engage the internal threads of the aperture. Often, the second thread has a conical configuration.

A bone screw may also be designed having a conical shank portion. The entire shank of the bone screw may be conical or the conical shank may be limited to only a portion of the shank. For instance, the shank portion that is disposed within an aperture of a bone plate may be conical while the bone engaging portion is not.

Other prior art designs have provided a conical thread from the bone engaging portion and increasing in diameter to the plate engaging portion of the shank of the fastener. The purpose of the conical thread is to self-start the threading of the fastener within the threaded aperture of the orthopedic plate. However, instead, as the conical threads become progressively larger and engage the female threads in the apertures of the orthopedic plate, undesirable cross-threading occurs. This results in a situation where the fastener and the fastener engagement with the plate is weakened. It may also impede the insertion of the screw fastener as the cross-threading may block the passage of the screw. The consequences of such cross-threading, whether full threading was possible or not, is that the screw will be very difficult if not impossible to remove from the plate. Quite often, that aperture of the plate in which the screw fastener is cross-threaded, is destroyed and rendered unavailable for use with another screw fastener.

SUMMARY OF THE INVENTION

A fastener in accordance with the present invention can be used as a monoaxial fastener in a plate or other device having an aperture with a female thread. In one aspect of the present invention, the fastener includes a single thread, the profile which is the same throughout the length of the fastener from the trailing end or proximal end at the bottom of the head (if there is a head) to the leading end or distal end of the fastener. Preferably, the pitch and depth of the thread is the same. However, that portion of the shank of the screw fastener—i.e., the plate engaging portion of the shank—has a different thickness than the remaining shaft of the screw fastener. More specifically, in this embodiment of the invention, the root diameter of the fastener shank (the thickness of the shank without the threads) is larger in the plate engaging portion, and this plate engaging portion is sized to lock with the plate as the bone engaging portion threads into the bone. In a preferred embodiment, there is no taper from the bone engaging portion to the plate engaging portion of the fastener shank. At most, there may be a chamfered step from one portion to the second portion. Preferably, the bone engaging portion of the fastener shank is sized to permit the thread to fit loosely between the female threads of the plate throughout the bone engaging portion of the shaft. This facilitates the threading process and avoids cross-threading.

In another embodiment, the fastener, in any one of the permeations discussed above, can be used in connection with a coupler having an internal thread, the coupler being positioned in a through-hole of a plate. Preferably, with a coupler, the fastener may not have a head so that the coupler can facilitate polyaxial movement of the fastener. Such a coupler might be a ball-shaped coupler or a coupler having spherical surfaces to permit polyaxial movement of the fastener. The fastener would self-thread into the internal thread of the coupler in the same fashion as described above. Once the plate engaging portion of the fastener—in this case, the coupler-engaging portion of the fastener—engages the internal thread of the coupler, the threading is tight between the coupler thread and the thread in the coupler engaging portion of the fastener shank.

In another aspect of the present invention an orthopedic screw for attachment to an orthopedic component in an orthopedic surgical procedure is provided. The orthopedic screw includes a shank, which includes a first portion and a second portion. The first portion having a first shank diameter and a first thread extending radially outward from the shank, said first thread defining a first thread diameter. The second portion includes a second shank diameter and a second thread extending radially outward from the second portion. The second thread has a second thread diameter. The second shank diameter and the second thread diameter are preferably smaller than the respective first shank diameter and first thread diameter.

The second thread has a thread height and a pitch and the first thread has a thread height and a pitch. In a preferred embodiment the thread height and pitch of the first thread are substantially equal to the thread height and pitch of the second thread, respectively.

The orthopedic screw may also include a distal tip. The distal tip having a third shank extending from the second portion remote from the first portion and including a third thread extending radially outward from the third shank. The third has a thread height and a pitch. In one aspect of the present invention the thread height and pitch of the third thread height substantially equal to the thread height and pitch of the first and second portions.

The distal tip may further include a first end remote from the second portion and at least one groove extending from the first end toward the second portion.

The orthopedic screw preferably includes a recess disposed in at least the head of the screw. The recess may be in the shape of a polygon.

In one preferred embodiment of the present invention the pitch of the first and second portion is approximately 1 millimeter. Additionally in one preferred embodiment of the present invention the thread height of the first and second portion is approximately 0.6 millimeters. Further the orthopedic screw may have a length between approximately 10 and 120 millimeters and with the first portion having a length between approximately 1 and 2.2 millimeters.

In another aspect of the present invention an orthopedic screw is provided for use in a surgical procedure. The orthopedic screw preferably includes a shank having a first portion and a second portion. The first portion preferably includes an engagement means adapted for engaging the screw relative to a second element. The second portion preferably includes an aligning means adapted for contacting the second element while being received within the second element. The aligning means further adapted for maintaining a correct relationship between the screw relative to the second element while being received within the second element until the second portion has surpassed the second element.

In another aspect of the present invention an orthopedic implant and an orthopedic screw are provided. The orthopedic implant preferably includes at least one aperture with internal threads. The orthopedic screw preferably includes a head, a first portion and a second portion. The first portion has a shank with a first shank diameter and a first thread. The first thread extending radially outward from the shank to define a thread diameter.

The second portion of the orthopedic screw has a shank with a second shank diameter and a second thread extending radially outward from the shank. The second shank diameter and the second thread diameter are preferably smaller than the first shank diameter and the second thread diameter.

Additionally, the second thread has a thread height and a pitch. The first thread also has a thread height and a pitch. In the most preferred embodiment, the thread height and pitch of the first thread are substantially equal to the thread height and pitch of the second thread, respectively In a further aspect of the present invention the second thread is adapted to be received in the aperture of the orthopedic implant and communicate with the internal threads of the orthopedic implant to maintain correct alignment between the orthopedic screw and the orthopedic implant. The first thread and the first shank diameter of said first portion are adapted to fully engage the internal threads of the at least one aperture of the orthopedic implant.

The orthopedic implant may be a bone plate or a coupler as well as additional implants.

In another aspect of the present invention, a method of attaching an orthopedic implant to a patient is described. The method preferably includes providing an orthopedic screw having a head, a first portion and a second portion. The first portion being in communication with the head and including a shank having a first inner diameter and a first thread extending radially outward from the shank. The first thread includes a first outer diameter.

The orthopedic screw further includes a second portion including a second shank having a second inner diameter and a second thread extending radially outward from the second portion. The second thread has a second outer diameter. The second inner diameter and the second outer diameter are smaller than the first inner diameter and the first outer diameter. The second thread has a thread height and a pitch and the first thread has a thread height and a pitch. The thread height and pitch of the first thread are substantially equal to the thread height and pitch of the second thread, respectively.

The method further includes providing an orthopedic implant, the implant having at least one aperture with an internal thread. Additional the method includes pre-drilling a hole into a bone to which the orthopedic implant will be attached to.

Next the orthopedic implant in placed in correct spatial relation relative to the pre-drilled hole. The orthopedic screw is than aligned with the aperture of the implant. The orthopedic screw through is than translated through the aperture and into the predrilled hole, wherein said second portion of the orthopedic screw contacts the internal thread of the aperture in order that the orthopedic screw maintains a predetermined spatial relationship with regard to the orthopedic implant. The screw is further translated through the aperture of the orthopedic implant, wherein the first portion contacts the internal thread of the orthopedic implant to lock the orthopedic screw relative to the orthopedic implant.

DETAILED DESCRIPTION

Figure 1:
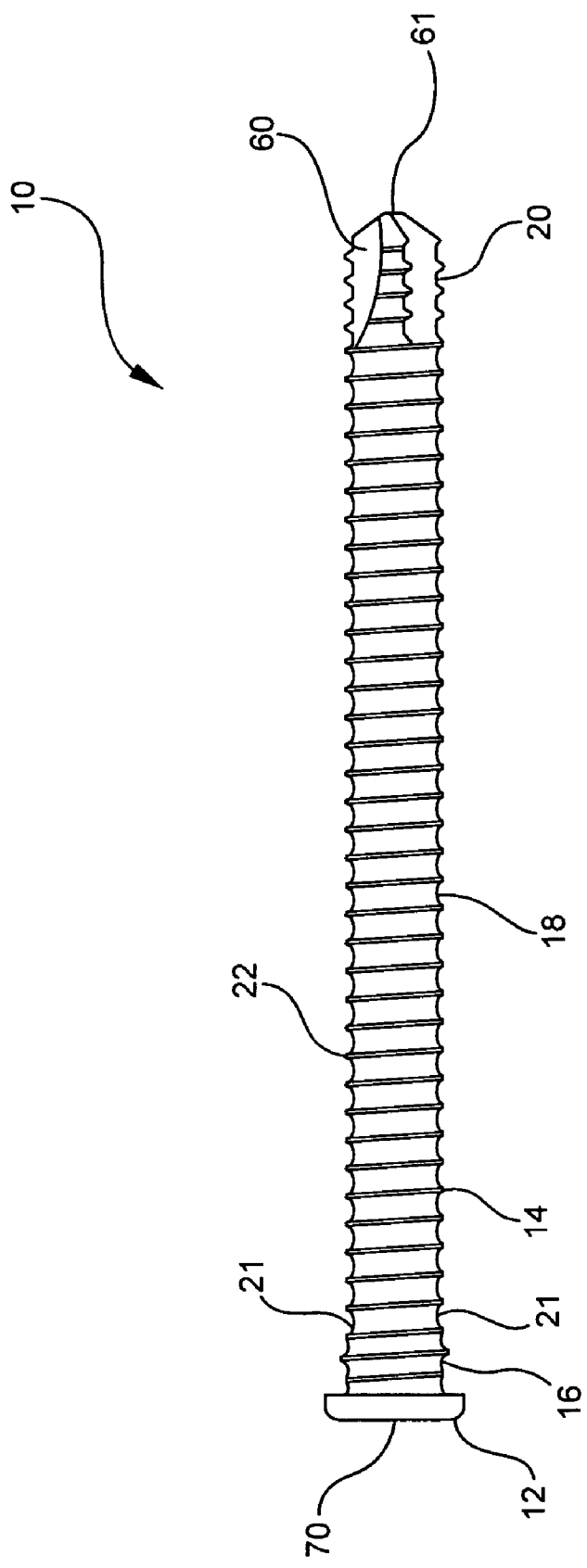
FIG. 1 is a side view of one embodiment of the present invention.

For the purposes of promoting and understanding the principles of the present invention, reference will now be made to the embodiment illustrated in the drawings and specification language will be used to describe the same. Nevertheless, by those skilled in the art, it will be understood that no limitation of the scope of the present invention is hereby intended and, further, changes in the illustrative device may be made to the preferred embodiments disclosed herein without deviating from the scope of the present invention.

As shown in FIG. 1, one embodiment of bone screw 10 includes a head 12 and a shank 14. Shank 14 extends downwardly from head 12 and preferably includes first portion 16, second portion 18 and distal tip 20. Shank 14 also preferably includes thread 22 extending radially outward from shank 14. Thread 22 extends radially outward from shank 22 as well as substantially continuous from the proximal end of first portion 16 to distal tip 20.

As is evident, first portion 16 resides in that portion of the shank 14 that engages the orthopedic implant, for instance a plate, when surgically implanted. There need not be exacting congruency in such engagement. The first portion 16 can partially engage the female threaded aperture of a plate, fully engage the female threaded aperture of a plate, or even extend beyond the bounds of the female threaded aperture of a plate. Preferably, a substantial portion of a threaded aperture in a plate is engaged by the first portion 16.

The second portion 18 of the bone screw 10 engages bone, though it may engage another orthopedic component used in connection with fracture fixation, joint reconstruction, spinal stabilization or fusion, or any other component within an orthopedic system. In either case, the length of the second portion 18 need not be in proportion to the first portion 16 as shown in the drawings, but rather can be of any suitable length (and other parameters) as may be suitable for a particular application.

Bone screw 10, as well as other elements which are described below, are preferably made from a biologically inert material, for example, any metal customarily used for surgical devices and particularly those used for bone screws and pins, such as titanium or stainless steel. Other suitable materials include, but are not limited to, alloys, composite materials, ceramics or carbon-fiber materials.

Figure 2:
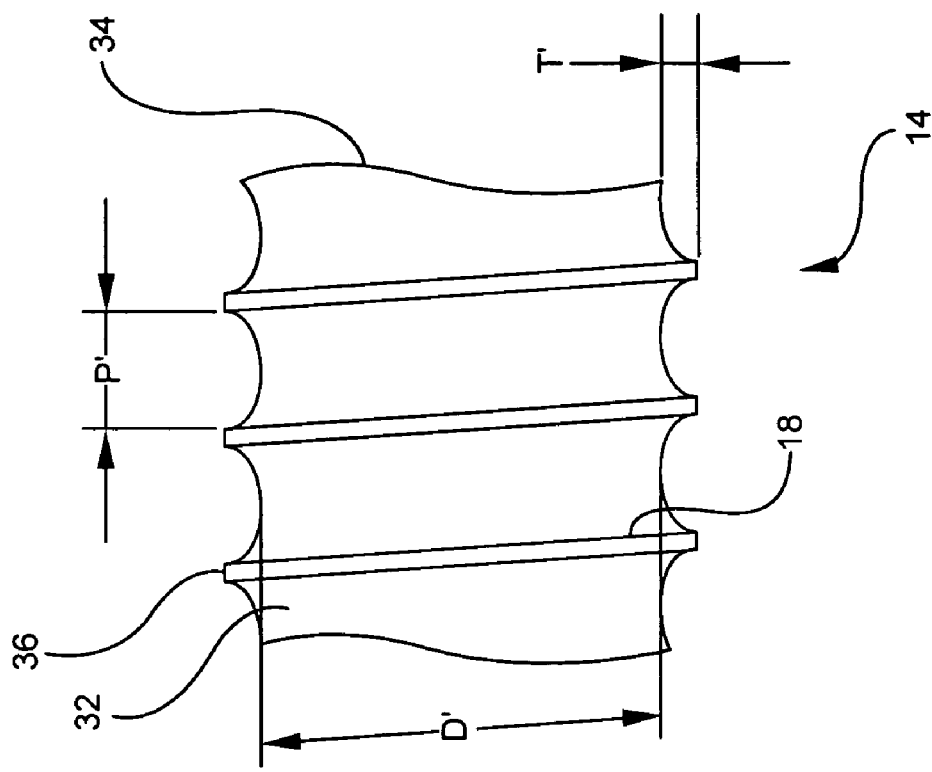
FIG. 2 is a cut-out view of the embodiment of FIG. 1 illustrating one embodiment of a first portion.

As shown in FIG. 2, first portion 16 of bone screw 10 includes first end 24 and second end 26. First end 24 is preferably in communication with head 12, though it need not be in every application. Preferably, the first portion 16 is not tapered from its first end 24 to its second end 26, but is instead of a constant diameter. Of course, a slight taper is still within the spirit of this preferred embodiment.

Shank 14 has a first diameter D in first portion 16. In a particularly preferred embodiment, first diameter D, representing the root diameter, is approximately between 2.9 millimeters and 5 millimeters. First portion 16 also includes first thread 30 which is preferably part of thread 22. First thread 30 has a pitch P and a thread height T. In one preferred embodiment, thread height T is approximately in a range between 0.25 millimeters and 3 millimeters, as measured from the shank 14. In addition, in one preferred embodiment, pitch P of first thread 30 is approximately between 0.8 millimeters and 1 millimeter.

Figure 3:
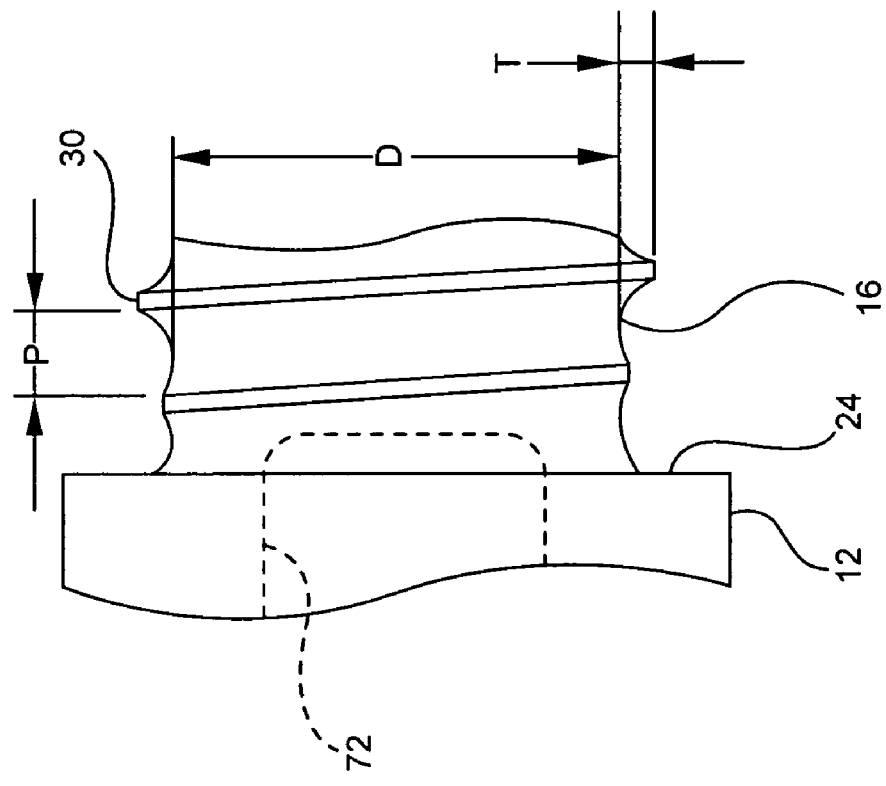
FIG. 3 is a cut-out view of the embodiment of FIG. 1 illustrating one embodiment of a second portion.

As shown in FIG. 3, second portion 18 of shank 14 includes a first end 32 and second end 34. First end 32, although not shown in FIG. 3, is preferably attached to and extends from second end 26 of first portion 16. Preferably, there is a chamfer 21 at the transition from the second end 26 of first portion 16 to the first end 32 of the second portion 18. Such a chamfer is a well-known engineering expedient to facilitate manufacture and to break sharp edges. Such chamfer is shown slightly in FIG. 1. Of course, there need not be direct communication between the first portion 16 and the second portion 18 at their respective ends. There may be some other portion in between, or a transition portion that is other than a chamfer.

Second portion 18 has a second diameter D', representing the root diameter. In a preferred embodiment, second diameter D' is between approximately 2.5 millimeters and 4.5 millimeters.

Second portion 18 of shank 14 also includes second thread 36 extending radially outward from shank 14. Second thread 36 is preferably part of thread 22 and is continuous with first thread 30. Second thread 36 has a pitch P' and a thread height T'. In one preferred embodiment of the present invention, pitch P' is approximately between 0.8 millimeters and 1 millimeter. Additionally, in one preferred embodiment of the present invention, thread height T' is approximately between 0.25 millimeters and 3 millimeters.

Therefore, in a preferred embodiment of the present invention, first diameter D is slightly larger than second diameter D'. However, pitch P and thread height T of first thread 30 is substantially equal to pitch P' and thread height T' of second thread 36, respectively. This arrangement facilitates the self-threading of the screw fastener 10 into a threaded aperture of an implant, for instance, a plate. Additionally, in one preferred embodiment, the outer diameter of second thread 36 is greater than diameter D in first portion 16. This facilitates that second thread 36 will engage internal threads of a second element as will be described below.

As shown in FIG. 1, the distal tip 20 may include surface modifications to facilitate the self-starting of the screw to the extent necessary. Thus, in the preferred embodiment, radial grooves or three equally-spaced grooves 10 which interrupt the continuous nature of the thread at the distal tip. Also provided is a bullet-nose chamfer 61 at the very tip. Of course, other well-known expedients may be practiced here as well.

The distal tip 20 may also be structured so as to have a different root diameter than the root diameter of the first portion 16 and a root diameter of the second portion 18. In this regard, any threads provided on the distal tip could be of the same pitch and height as that of the first portion 16 and second portion 18 (or either of them), or could differ.

In a further description of one embodiment of bone screw 10, head 12 preferably includes recess 70 to facilitate the engagement of a device tool. Hexagon, slotted, diamond shaped, star shaped or other geometric structures can be used, with star-shaped being preferred. In one preferred embodiment, the third thread diameter, i.e., diameter of the thread I the distal tip, is less than the first shank diameter. In addition, in an alternate embodiment, a protruding abutment may be provided on head 12 to mate with a tool.

The diameter of the first portion 16 is, in a preferred embodiment, substantially constant throughout the length of the first portion 16. However, in another preferred embodiment, the first portion 16 may have a diameter that is constant along a substantial portion of the first portion 16. Likewise, in a preferred embodiment, the second portion 18 includes a constant diameter. The constant diameter of the second portion 18 may be, in a preferred embodiment, nonconstant, as the distal tip 20 may have a different diameter. It is also contemplated in preferred embodiments that the first portion 18 has a constant diameter along substantially the length of the second portion 18. The second portion 18 may also have more than one constant diameter portion, each having a different diameter. The second portion 18 may also have a constant diameter portion and a tapered diameter portion. The design criteria to balance in arranging the structure of the first portion 16 and the second portion 18 is the self-threading function performed by the second portion 18, and the subsequent full-threading by the first portion 16. The overall diameter or thread diameter of the screw fastener will also take into account the thread height.

Figure 4:
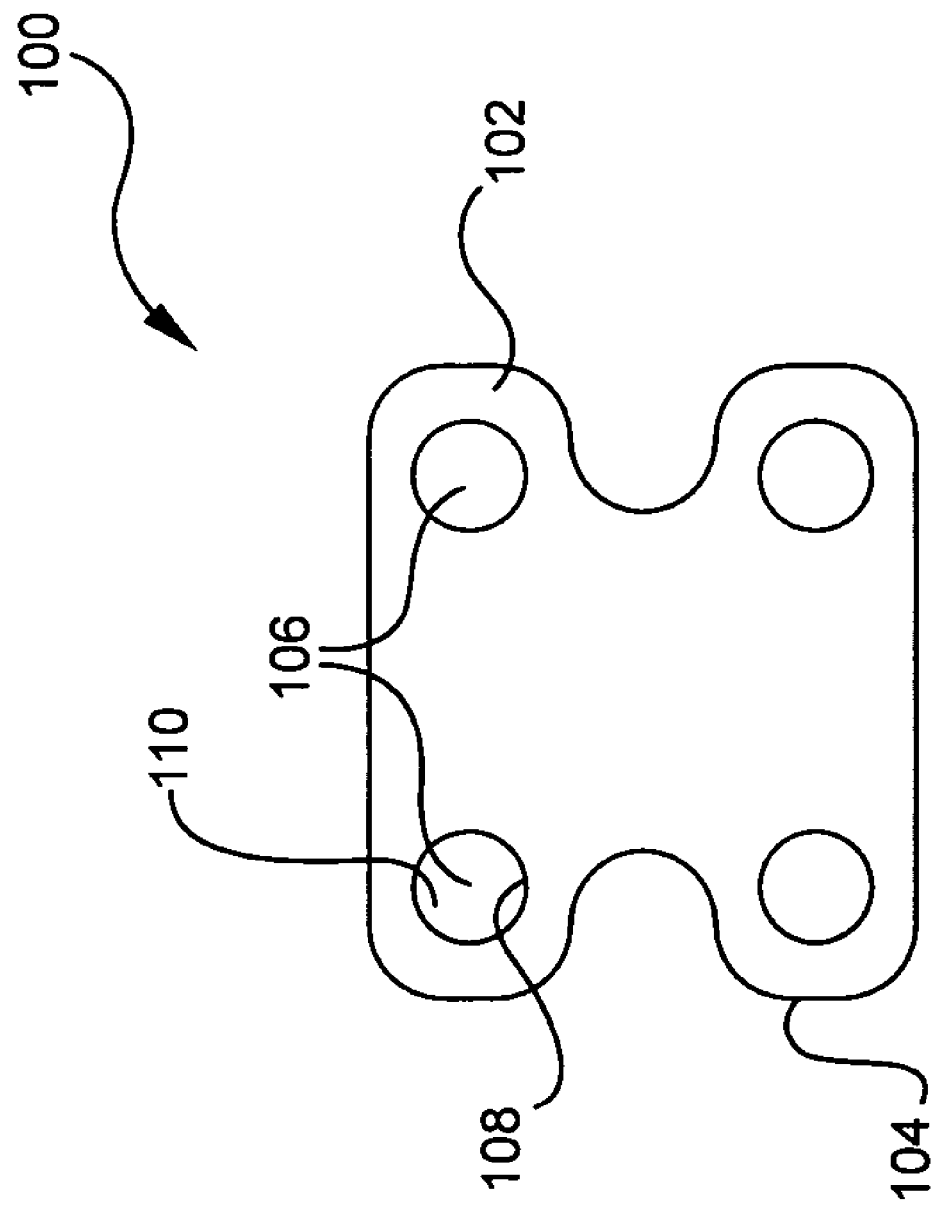
FIG. 4 is a top view of one embodiment of an orthopedic implant used in combination with the embodiment of FIG. 1.

Bone screw 10 is most preferably adapted for use with orthopedic implants, especially bone plates. An example of one such bone plate is shown in FIG. 4. Bone plate 100 includes front surface 102 and rear surface 104. As further discussed, rear surface 104 has no gravitational relationship except that rear surface 104, as discussed herein, is configured to face the structure to which bone plate 100 will be attached to. Bone plate 100 also preferably includes at least one aperture 106 extending from front surface 102 to rear surface 104 therethrough. Although bone plate 100 is shown with four apertures in FIG. 4, often various bone plates, as well as additional implants, may have more or less apertures.

Apertures 106 of plate 100 preferably include interior threads 108 extending inwardly from interior wall 110 of aperture 106. Threads 108 are adapted for mating with at least a portion of the threads of bone screw 10.

Figure 5:
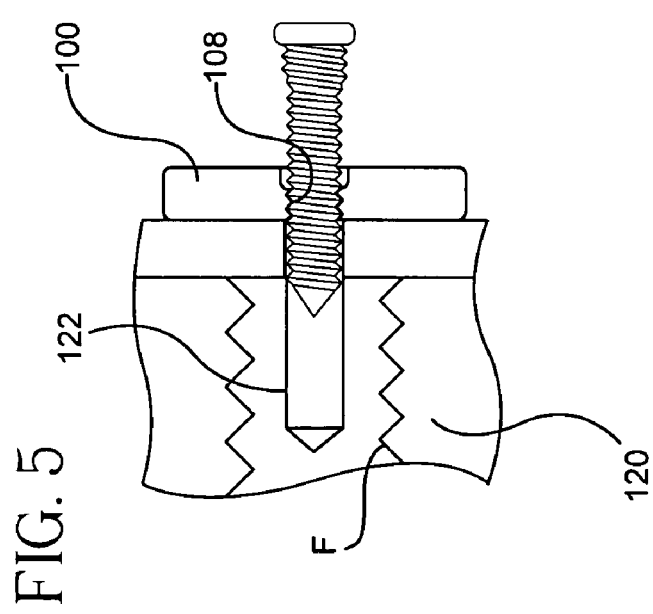
FIG. 5 is a side view of the orthopedic implant of FIG. 4 in a method of use.

In a method of use, as shown in FIG. 5, bone plate 100 is placed adjacent to a bone 120. The bone 120 may be a fractured femur, humerus or any other bone. Plate 100 may span a fracture or fractures, illustrated as F on FIG. 5. The bone may be a vertebral body or bodies, with the plate spanning the intervertebral space. The bone may, of course, be any other bone or bone segment that is involved in an orthopedic treatment.

Either prior to or after the bone plate is placed against bone 120. Pilot hole 122 is pre-drilled into bone 120. Hole 122 preferably has a cross-section which is preferably at least less than the diameter of threads 22 of bone screw 10 and preferably substantially equal to the diameter of the second portion 18. Of course, with reference to thread 22, part of thread 22 may preferably have a cross section less than the cross section of the diameter at least in the distal tip 20 region. In order to affix bone plate 100 to bone 120, bone screw 10 is placed within aperture 106 and translated downward or into bone 120 via hole 122 with distal tip 20 first being introduced to the bone 120. An additional set of screws having a different configuration may be used to hold the bone plate 100 in contact with bone 120.

Figure 6:
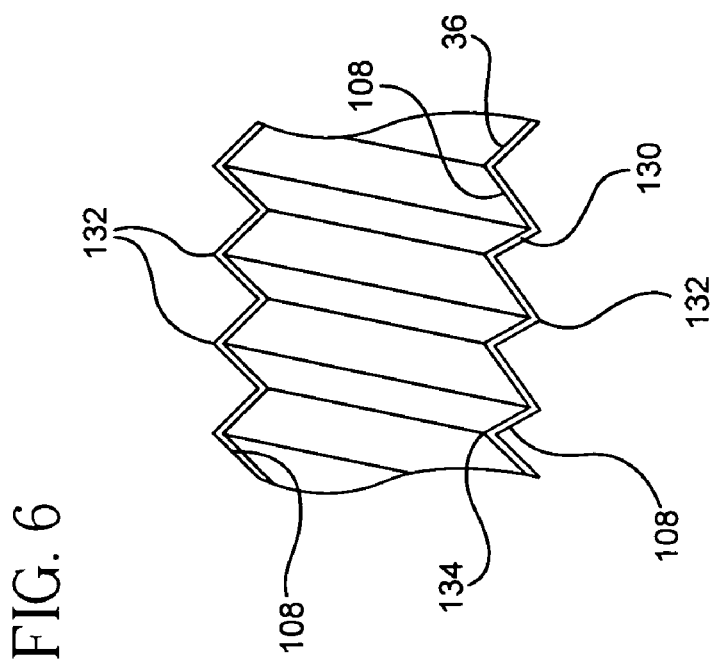
FIG. 6 is an enlarged cross-sectional view of the threads, screw and the female threads of an orthopedic implant of FIG. 4.

In a preferred embodiment of the present invention, second portion 18 has a shank diameter which enables second thread 36 to enter the boundary of the internal thread 108 of the bone plate 100. Although second thread 36 contacts internal threads 108 of aperture 106, the threads do not fully mate with each other, i.e., come into full contact with one another. In other words, the diameter D' of the second portion 18 will not tighten against the internal threads 108. FIG. 6 illustrates this "self-tightening." For instance, as shown in FIG. 6, second thread 36, when placed symmetrical relative to internal threads 108, leaves gaps 130 between the two threads. Therefore, although bone screw 10 may be pushed against either side of aperture 106 and fully contact internal threads 108 on one side, it is not possible for second threads 36 to fully lock within aperture 106. However, the threads 36 along with second diameter D' do have a large enough cross-sectional diameter to enable apexes 132 of thread 36 to enter the valleys 134 of internal thread 108. This allows a spatial relationship between the two threads that guides bone screw 10 through bone plate 100 while reducing the possibility of cross-threading the threads.

To the extent that the distal tip 20 of the screw fastener 10 includes a different root diameter than the second portion 18 and the same threads in terms of pitch and height, the sizing of the different diameter at the distal tip will determine whether the threads in the distal tip area will enter the valleys 134 of the internal thread 108.

Figure 8:
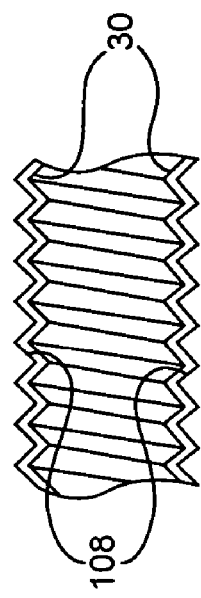
FIG. 8 is an enlarged cross-sectional view of the threads illustrating the cooperation between the plate engaging portion of a bone screw and the female threads of an orthopedic implant of FIG. 7.
Figure 7:
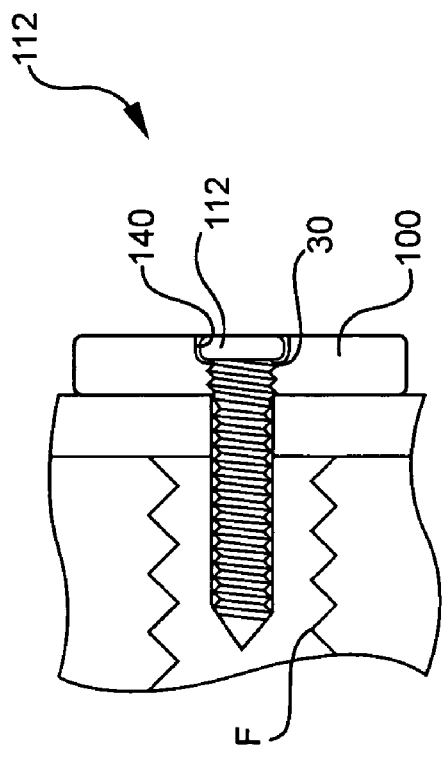
FIG. 7 is a side view of an orthopedic implant of FIG. 4, illustrating the fastener and further threaded into its fastened position.

As such, bone screw 10 is translated downward into hole 122 of bone 100 until first portion 16 of bone screw 10 comes in contact with internal threads 108. First portion 16 has a first diameter D which is specifically adapted for not only allowing thread 30 to come into contact with internal thread 108 of bone plate 100, but also to lock the bone plate relative to the bone screw, as shown in FIG. 7. This result is highlighted in FIG. 8, in which it can be easily seen that thread 30, when placed within aperture 106, contacts internal threads 108 to establish the integrity of the desired threading forces.

Preferably, bone screw 10 is translated through bone plate 100 and into bone 120 until head 12 contacts bone plate 100. In a preferred embodiment, bone plate 100 includes a recess or countersink 140 designed for receiving head 12 of the bone screw. This configuration enables the top surface of head 12 to be flush with the front surface 102 of the bone plate.

Although the present invention has been described with reference to a bone plate having internal threads directly attached thereto, in alternate embodiments, an orthopedic implant may include a coupler that is disposed within apertures of the bone plate. A coupler may be in the form of an insert that functions as a blocker to prevent the screw fastener from backing out of a plate or other orthopedic implant. Such an insert is shown and described in U.S. patent application Ser. No. 10/999,132 entitled Device For Connecting A Screw To A Support Plate by inventor Robert Porcher, and filed on Nov. 29, 2004, the entire disclosure of which is incorporated herein by references as if fully set forth herein. The coupler may also be an insert that locks to a plate or other orthopedic implant through the deformation of the insert upon tightening of the screw fastener.

A coupler may also be in the form of a ring or other expedient that facilitates the polyaxial placement of a screw fastener through a plate or other implant into a bone. With such an arrangement, a screw fastener can be placed through a plate at an angle to obtain better bony purchase, to facilitate ease of implantation procedure, to avoid fractured portions of the bone, or for any other reason. Such a ring could be slotted to allow contraction for insertion into a plate aperture and/or expansion against the plate aperture as the threaded fastener 10 is driven into place. The ring might also be unslotted. With the use of a ring, insert or other coupler, the coupler itself would preferably carry the internal threads, and the aperture of the implant in which the coupler resides would not be threaded, though it could be in a particular embodiment.

Figure 9:
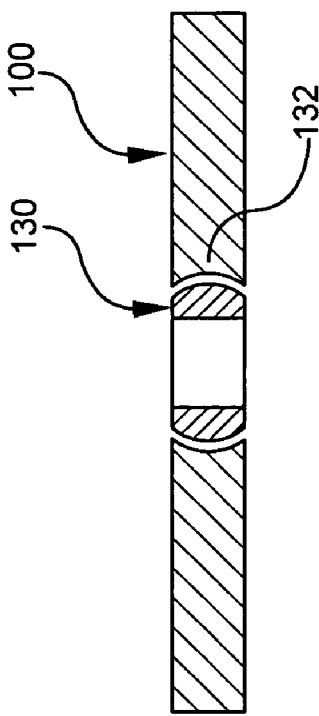
FIG. 9 illustrates an alternate embodiment of the orthopedic implant used in the present invention.

FIG. 9 illustrates a ring 130 that can be polyaxially arranged within the plate 100 to permit a screw fastener to be inserted through the plate and into a bone at an angle. The arcuate surfaces 132 of the ring 130 facilitating such arrangement. Of course, any other arrangement of a coupler can be provided.

An extraction tool for extracting the insert from a plate is disclosed in U.S. application entitled Bone Plating Implants, Instruments And Methods by inventors Christian Lutz, Yves Crozet and Rene Wirth, and filed on Nov. 30, 2004, such application being incorporated herein by reference as if fully set forth herein.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An orthopedic system comprising:
   an orthopedic implant having at least one aperture with internal threads;
   an orthopedic screw having a head; a first portion in communication with said head, said first portion having a shank with a first shank diameter and a first thread extending radially outward from said shank to define a thread diameter, said orthopedic screw having a second portion having a shank with a second shank diameter and a second thread extending radially outward from said second shank to define a second thread diameter, said orthopedic screw having a distal tip, said second shank diameter and said second thread diameter being smaller than said first shank diameter and said first thread diameter respectively;

said second thread having a thread height and a pitch, and said first thread having a thread height and a pitch, wherein said thread height and pitch of said first thread are substantially equal to said thread height and pitch of said second thread, respectively;

wherein said second thread is adapted to be received in said aperture of said orthopedic implant and communicate with said internal threads of said orthopedic implant to maintain correct alignment between said orthopedic screw and said orthopedic implant, said first thread and said first shank diameter of said first portion being adapted to fully engage said internal threads of said at least one aperture of said orthopedic implant;

wherein said second thread diameter is greater than said first shank diameter; and wherein the first and second threads have the same thread profile.

2. The orthopedic system according to claim 1, wherein said orthopedic implant is a bone plate.

3. The orthopedic system according to claim 1, wherein said orthopedic implant includes a coupler.

4. The orthopedic system according to claim 1, wherein said orthopedic screw has a thread height and pitch at said distal tip which are substantially equal to the thread height and pitch of said first and second portions.

5. The orthopedic system according to claim 4, wherein said orthopedic screw distal tip includes a tapered portion.

6. The orthopedic system according to claim 1, wherein said distal tip of the orthopedic screw includes a first end remote from said second portion, said distal tip further including at least one groove extending from said first end toward said second portion.

7. The orthopedic system according to claim 1, wherein said orthopedic screw includes a head, said head having a recess.

8. The orthopedic system according to claim 7, wherein said recess is in the shape of a star.

9. The orthopedic system according to claim 1, wherein said orthopedic screw has a pitch which is approximately between 0.8 millimeters and 1 millimeter.

10. The orthopedic system according to claim 1, wherein said thread height is approximately between 0.25 millimeters and 3 millimeters.

11. The orthopedic system according to claim 1, wherein said orthopedic screw is self-drilling.

12. The orthopedic system according to claim 1, wherein the orthopedic screw has a length between approximately between 10 millimeters and 120 millimeters and said first portion has a length between 1 millimeter and 2.2 millimeters.

13. The orthopedic system according to claim 1 wherein the orthopedic screw further includes a transition portion between said first and second portions, wherein the transition portion is chamfered.

14. The orthopedic system according to claim 1 wherein said orthopedic screw further includes a head, and wherein said head has a bottom surface that can be mounted flush with an outer surface of the orthopedic implant.

15. The orthopedic system according to claim 1, wherein said orthopedic screw first thread and said second thread are continuous.

16. The orthopedic system according to claim 1, wherein said orthopedic screw thread height and pitch of said distal tip thereof is substantially equal to said thread heights and pitches, respectively, of said first and second threads, respectively.

17. The orthopedic system according to claim 1, wherein the first shank diameter of the orthopedic screw has a substantially constant first diameter and said second shank diameter has a substantially constant second diameter.

18. The orthopedic screw according to claim 1, wherein the screw further includes a head, and wherein said head is flush with the bone plate.

19. A method of attaching an orthopedic implant to a patient, the method comprising:

providing an orthopedic screw having a head, a first portion in communication with said head, said first portion including a first shank having first and second ends, a first root diameter and a first thread extending radially outward from said first shank, said first root diameter being substantially constant between the first and second ends of the first shank, said first thread with a thread profile and defining a first outer diameter, said orthopedic screw further having a second portion including a second shank having first and second ends, a second root diameter and a second thread extending radially outward from said second portion, said second root diameter being substantially constant between the first and second ends of the second shank, said second thread having the same thread profile as the first thread and having a second outer diameter, said second root diameter and said second outer diameter being smaller than said first root diameter and said first outer diameter, and said second thread having a thread height and a pitch, said first thread having a thread height and a pitch, wherein said thread height and pitch of said first thread are substantially equal to the thread height and pitch of said second thread, respectively;

providing an orthopedic implant, said implant having at least one aperture with an internal thread;

pre-drilling a hole into a bone to which said orthopedic implant will be attached to;

aligning said orthopedic implant in correct spatial relation to said pre-drilled hole;

aligning said orthopedic screw with said aperture of said implant and translating said orthopedic screw through said aperture and into said predrilled hole, wherein said second portion of said orthopedic screw contacts said internal thread of said aperture in order that said orthopedic screw maintains a predetermined spatial relationship with regard to said orthopedic implant;

translating said orthopedic screw further through said aperture of said orthopedic implant; and wherein said first portion contacts said internal thread of said orthopedic implant to lock said orthopedic screw relative to said orthopedic implant.

20. The method of claim 19 wherein the orthopedic screw further comprises a distal tip, said distal tip having a third shank with a third root diameter and said distal tip including a third thread extending radially outward from said third shank, said third thread having a thread height and a pitch.

21. The method of claim 19 wherein the orthopedic screw has a thread height and pitch of said distal tip are substantially equal to said thread height and pitch of said first and second portions.

22. The method of to claim 21, wherein said distal tip of the orthopedic screw includes a first end remote from said second portion, said distal tip further including at least one groove extending from said first end toward said second portion.

23. The method of claim 19, wherein the orthopedic screw second outer diameter is greater than said first root diameter.

* * * * *

UNITED STATES PATENT AND TRADEMARK OFFICE
CERTIFICATE OF CORRECTION

PATENT NO.         : 7,799,062 B2
APPLICATION NO.    : 11/000098
DATED              : September 21, 2010
INVENTOR(S)        : Yves Stephane Crozet and Partic Sommer It is certified that error appears in the above-identified patent and that said Letters Patent is hereby corrected as shown below:

Column 2, line 15, delete "is" and insert therefor --are--.
Column 2, line 51, delete "having" and insert therefor --has--.
Column 2, line 66, delete "having" and insert therefor --has--.
Column 3, line 4, after "height" insert therefor --are--.
Column 3, line 28, after "means" insert therefor --is--.
Column 3, line 38, delete "extending" and insert therefor --extends--.
Column 3, line 64, delete "being" and insert --is--, and delete "including" and insert therefor --includes--.
Column 4, line 13, delete "additional" and insert therefor --additionally--.
Column 4, line 18, delete "than" and insert therefor --then--.
Column 4, line 19, delete "through", and delete "than" and insert therefor --then--.
Column 5, line 25, delete "are" and insert therefor --is--,
Column 6, line 9, delete "is" and insert therefor --are--.
Column 6, line 21, delete "which".
Column 8, line 17, before "Device" insert --"--.
Column 8, line 18, after "Plate" insert --"--.
Column 8, line 41, delete "facilitating" and insert therefor --facilitate--.
Column 8, line 45, before "Bone" insert --"--.
Column 8, line 46, after "Methods" insert --"--.
Column 10, line 3, delete "is" and insert therefor --are--.
Column 10, line 48, "predrilled" should read --pre-drilled--.
Column 11, line 1, after "of", delete "to".

Signed and Sealed this
Fifteenth Day of November, 2011

David J. Kappos
*Director of the United States Patent and Trademark Office*